(12) United States Patent
Kim et al.

(10) Patent No.: US 9,588,146 B2
(45) Date of Patent: Mar. 7, 2017

(54) ELECTRODE FOR MEASURING BIOSIGNAL AND BIOSIGNAL MEASUREMENT DEVICE

(71) Applicants: Samsung Electronics Co., Ltd., Suwon-si (KR); SNU R&DB FOUNDATION, Seoul (KR)

(72) Inventors: Youn Ho Kim, Hwaseong-si (KR); Kun Soo Shin, Seongnam-si (KR); Kwang Suk Park, Seoul (KR); Jeong Su Lee, Seoul (KR); Yong Gyu Lim, Seoul (KR)

(73) Assignees: Samsung Electronics Co., Ltd., Suwon-si (KR); SNU R&DB FOUNDATION, Seoul (KR)

( * ) Notice: Subject to any disclaimer, the term of this patent is extended or adjusted under 35 U.S.C. 154(b) by 197 days.

(21) Appl. No.: 14/454,280

(22) Filed: Aug. 7, 2014

(65) Prior Publication Data

US 2015/0042312 A1 Feb. 12, 2015

(30) Foreign Application Priority Data

Aug. 8, 2013 (KR) .......................... 10-2013-0094181

(51) Int. Cl.
*G01R 15/16* (2006.01)
*G01R 1/20* (2006.01)
(Continued)

(52) U.S. Cl.
CPC .......... *G01R 15/16* (2013.01); *A61B 5/04284* (2013.01); *G01R 1/203* (2013.01);
(Continued)

(58) Field of Classification Search
CPC . A61B 5/0478; A61B 5/0006; A61B 5/04085; A61B 5/0402; A61B 5/0408; A61B 5/024; A61B 5/04087; A61B 5/04284; A61B 5/02438; A61B 5/0245; A61B 5/04014; A61B 2562/0214; A61B 2562/182; A61B 5/053; A61B 2562/164; A61B 2562/166; A61B 2562/16; A61B 5/4836; G01R 15/16; G01R 1/06794; G01R 1/18; G01R 1/203; G01R 27/2605
See application file for complete search history.

(56) References Cited

U.S. PATENT DOCUMENTS 5,194,020 A * 3/1993 Voltz .................... H01R 13/514
439/540.1
6,961,601 B2 * 11/2005 Matthews ............ A61B 5/0408
600/372
(Continued)

FOREIGN PATENT DOCUMENTS

JP 11-113866 A 4/1999
JP 2011-223 A 1/2011
(Continued)

*Primary Examiner* — Vinh Nguyen
(74) *Attorney, Agent, or Firm* — NSIP Law (57) ABSTRACT

Disclosed are a biosignal measurement device and a capacitively-coupled active electrode. The capacitively-coupled active electrode includes an electrode face configured to form capacitive coupling with a subject in a non-contact manner to detect a biosignal, and a pre-amplifier disposed on a rear side of the electrode face and embedded in a porous insulator.

19 Claims, 9 Drawing Sheets

(51) Int. Cl.
    *A61B 5/0428*     (2006.01)
    *A61B 5/04*     (2006.01)
    *A61B 5/0478*     (2006.01)
    *A61B 5/0492*     (2006.01)
    *A61B 5/0496*     (2006.01)

(52) U.S. Cl.
    CPC ......... *A61B 5/04004* (2013.01); *A61B 5/0478* (2013.01); *A61B 5/0492* (2013.01); *A61B 5/0496* (2013.01); *A61B 2562/0214* (2013.01)

(56) References Cited

U.S. PATENT DOCUMENTS

| | | | |
|---|---|---|---|
| 8,825,128 B2 * | 9/2014 | Ylostalo | 600/372 |
| 2004/0164749 A1 * | 8/2004 | Dingwall | G07B 15/00 |
| | | | 324/662 |
| 2004/0254435 A1 | 12/2004 | Mathews et al. | |
| 2007/0015984 A1 * | 1/2007 | Yeo | A61B 5/04087 |
| | | | 600/372 |
| 2008/0150631 A1 * | 6/2008 | Kim | A61B 5/04284 |
| | | | 330/103 |
| 2012/0116198 A1 * | 5/2012 | Veen | A61B 5/04284 |
| | | | 600/372 |

FOREIGN PATENT DOCUMENTS

| | | |
|---|---|---|
| JP | 2011-36524 A | 2/2011 |
| JP | 2012-120705 A | 6/2012 |
| KR | 10-2006-0050892 A | 5/2006 |
| KR | 20-0416389 Y1 | 5/2006 |
| KR | 10-2009-0131542 A | 12/2009 |

\* cited by examiner

ELECTRODE FOR MEASURING BIOSIGNAL AND BIOSIGNAL MEASUREMENT DEVICE

CROSS-REFERENCE TO RELATED APPLICATION(S)

This application claims the benefit under 35 USC 119(a) of Korean Patent Application No. 10-2013-0094181 filed on Aug. 8, 2013, in the Korean Intellectual Property Office, the entire disclosure of which is incorporated herein by reference for all purposes.

BACKGROUND

1. Field

The following description relates to an electrode for measuring a biosignal and to a biosignal measurement device.

2. Description of Related Art

Information technology (IT) networks, such as the Internet, a mobile phone, a bi-directional cable television (TV), and the like may be used to improve the sharing of medical information between healthcare providers and patients.

For example, Ubiquitous health (U-health) refers to an IT network service that provides healthcare service and medical treatments, such as diagnosis, treatments, and a real-time monitoring of a patient's health condition, by connecting a patient to a doctor without restrictions placed on time and space by requiring the patient to meet with the doctor in person.

An electrocardiogram (ECG) measurement device is used by healthcare providers to measure a biosignal related to an electric activity that occurs inside the body during the beating of a heart. ECG electrodes that are used in hospitals generally include a conductive gel. For this type of ECG electrodes, a healthcare technician places the ECG electrodes directly on the skin of a patient in order to obtain an ECG, which is a record of waves related to electrical impulses produced during the beating of a patient's heart.

An ECG measurement device that may be used outside of a hospital environment is desirable to allow patients to use the U-health service and other IT network-based health services.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a capacitively-coupled active electrode including an electrode face configured to detect a biosignal, a pre-amplifier configured to amplify the biosignal, a shield configured to surround the electrode face and the pre-amplifier, and an insulator that is flexible and configured to support the shield on the electrode face.

The insulator may include a material having mechanical strength to maintain a space predefined between the electrode face and the shield.

The insulator may include a material that includes an air layer.

The insulator may include a porous material in which air bubbles are dispersed.

The insulator may include at least one of silicon foam, urethane foam, silicone, urethane, rubber, and polyvinyl chloride (PVC).

The insulator may include a material having a dielectric constant less than 4 at STP.

The shield may include a flexible material that conforms to a shape of the insulator.

The shield may include a conductive sheet that surrounds the insulator.

The general aspect of the electrode may further include a conductive foam configured to conform to an irregular contact surface of a target.

The electrode face may include a flexible printed circuit board (FPCB) that conforms to a shape of the insulator.

The capacitively-coupled active electrode may be a non-contact electrode without a conductive gel disposed on the electrode face.

In another general aspect, there is provided a biosignal measurement device including a capacitively-coupled active electrode comprising an insulator that is flexible and configured to support a shield that surrounds a pre-amplifier on an electrode face configured to detect a biosignal, and a signal processing unit configured to extract a measurement result by processing the biosignal.

The insulator may include a material having mechanical strength to maintain a space predefined between the electrode face and the shield.

The insulator may include a material comprising an air layer.

The insulator may include a porous material in which air bubbles are dispersed.

The insulator may include at least one of silicon foam, urethane foam, silicone, urethane, rubber, and polyvinyl chloride (PVC).

The insulator may include a material having a dielectric constant less than 4 at STP.

The shield may include a flexible material that conforms to a shape of the insulator.

The shield may include a conductive sheet that surrounds the insulator.

The capacitively-coupled active electrode may further include a conductive foam configured to conform to an irregular contact surface of a target to establish a non-contact capacitive coupling.

The electrode face may include a flexible printed circuit board (FPCB) that conforms to a shape of the insulator.

The capacitively-coupled active electrode may be a non-contact electrode without a conductive gel disposed on the electrode face.

In another general aspect, there is provided a capacitively-coupled electrode including an electrode face configured to form a capacitive coupling with a subject in a non-contact manner to detect a biosignal, and a pre-amplifier disposed on a rear side of the electrode face and embedded in a porous insulator.

The general aspect of the capacitively-coupled electrode may further include a shield covering the porous insulator such that the pre-amplifier is encapsulated between the rear side of the electrode face and the shield.

The shield may include a flexible material that conforms to a shape of the porous insulator.

Other features and aspects will be apparent from the following detailed description, the drawings, and the claims.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Non-invasive biopotential sensors may be applied to skin surfaces to measure biosignals. To ensure a good resistive contact to the skin, a conductive gel is often used. Thus, such a biopotential sensor is referred to as a wet electrode. ECG electrodes that are used in hospitals generally include a conductive gel. However, an ECG of a patient may be obtained without using a conductive gel in a noncontact manner. For example, an ECG of a patient may be obtained in a state in which a patient is wearing clothes, for example.

A technique for measuring biosignals in a noncontact manner without the use of a conductive gel can facilitate the measurement of biosignals by users who are not healthcare professionals. Further, such technique can enhance services provided by the U-health and other IT network-based healthcare services by allowing the monitoring of a patient's biosignals without having the patient physically brought to a hospital.

Figure 1:
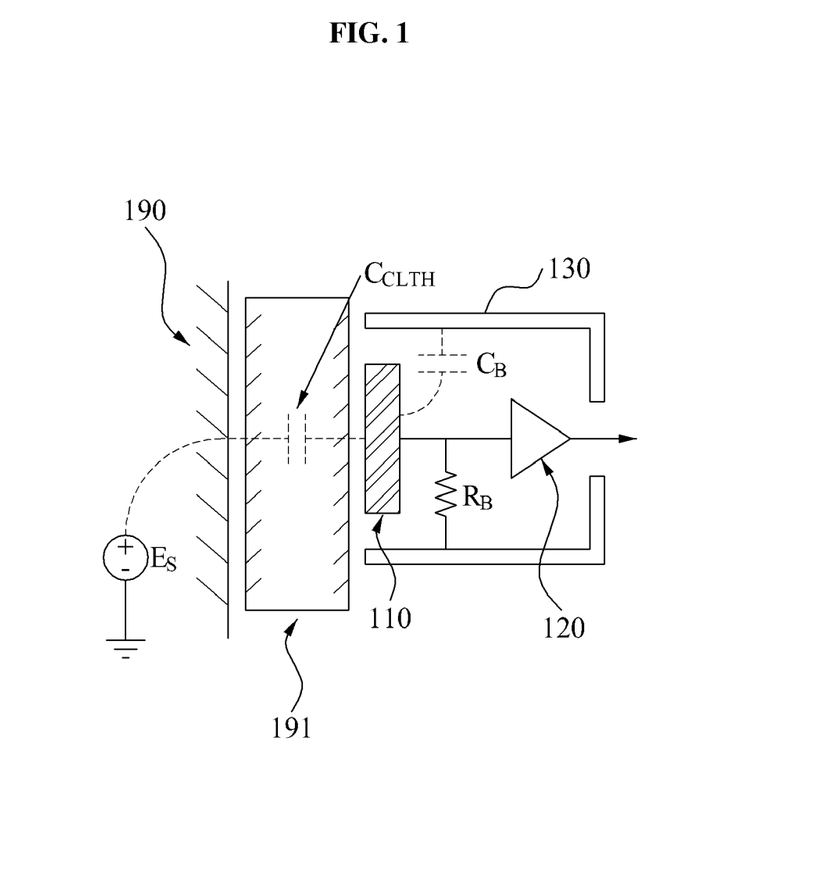
FIG. 1 is a circuit diagram illustrating an example of a capacitively-coupled electrode (CCE).

FIG. 1 illustrates an example of a capacitively-coupled electrode (CCE). The illustrated CCE is an active capacitively-coupled noncontact electrode (CCNE). An active electrode refers to an electrode that does not use an electrolyte or a conductive gel to obtain a resistive contact to a subject, such as the skin of a patient. Rather, active electrodes may employ an impedance transformation at a sensing site via active electronics. Further, the detection of the human biosignals may be obtained based on capacitive coupling, without the resistive coupling to the skin.

Referring to FIG. 1, the CCE includes an electrode face 110 implemented with a metal plate, a pre-amplifier 120 provided at the rear of the electrode face 110, and a shield 130 configured to surround the electrode face 110 and a rear surface of the electrode surface 110. In the event that a clothing 191 is present between the electrode face 110 and a human body 190, a capacitive coupling, labeled as $C_{CLTH}$ in FIG. 1, may be established between the skin 190 and the electrode face 110.

According to one example, a resistor with a resistance $R_B$ may be connected between the shield 130 and an input terminal of the pre-amplifier 120 in order to stabilize an amplifier by flowing bias current in an amplifier element, for example, a transistor or an operation amplifier of the pre-amplifier 120. In the event that a biosignal is measured using an indirect contact, a high resistance, for example, of 2G $\Omega$ or more may be applied to increase the input impedance of the amplifier. In this example, stray capacitance $C_B$ may be present between the electrode face 110 and a ground. The $E_S$ in FIG. 1 denotes a signal source obtained by modeling the biosignal of the human body 190. The signal source has a unit of "V".

The CCE according to examples described herein may generate a capacitive coupling between a skin and an electrode face through an indirect contact between the skin of a human body and a piece of clothing. A measurement result of the biosignal may be obtained by extracting a differential component from two signals obtained from two active electrodes and then amplifying and filtering the extracted differential component using a differential amplifier. Examples of measurement results obtained by measuring the biosignal include an electrocardiogram (ECG) waveform. Other biosignals that may be obtained include an electrooculogram (EOG), an electromyogram (EMG), an electroencephalogram (EEG) and the like.

A ground plate may ground the human body through capacitive coupling using clothes, without directly contacting with the skin of the human body. Using a CCE and an indirect contact ground plate, a biosignal may be measured without using any direct contact between the human body and the measurement equipment. In general, an electrode face and a shield may be designed using a metal material that is hardened at a predetermined interval in order to minimize a change in parasitic capacitance $C_B$.

Figure 2:
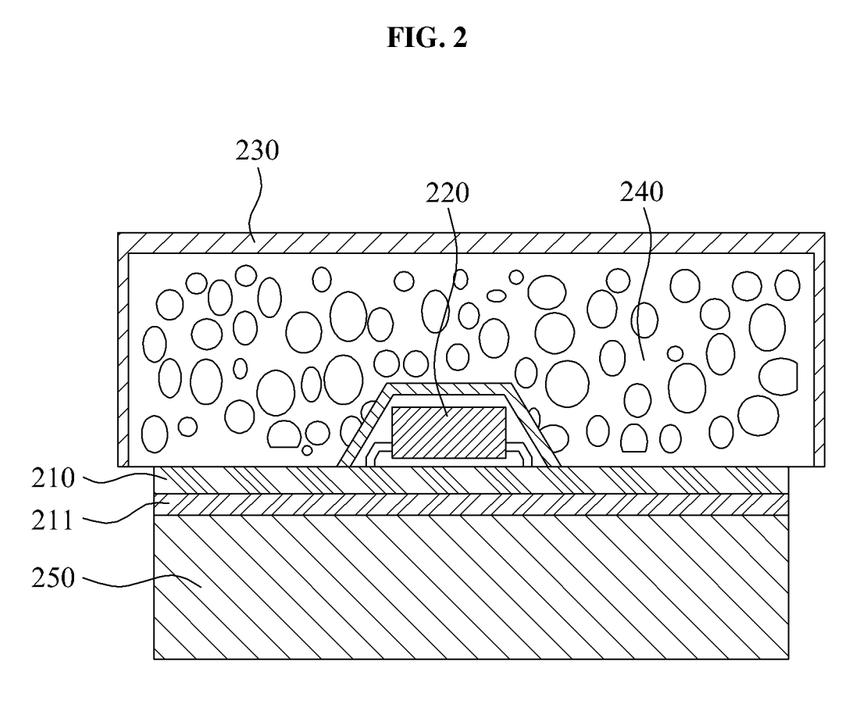
FIG. 2 is a cross-sectional view illustrating an example of a flexible CCE (FCCE).

FIG. 2 illustrates an example of a flexible CCE (FCCE). Referring to FIG. 2, the FCCE includes an electrode face 210, a pre-amplifier 220, a shield 230, an insulator 240, and a conductive foam 250.

The electrode face 210 may be made of a conductive material such as, for example, a metal plate. The electrode face 210 may be used to detect a biosignal. The electrode face 210 may include a flexible printed circuit board (FPCB) 211, and may be made of a flexible material. For example, the FPCB 211 may be flexible enough to conform to the shape of the insulator in the event that some portion of the insulator is deformed due to external stress.

The pre-amplifier 220 may amplify a biosignal detected by the electrode face 210. For example, the pre-amplifier 220 may be configured as a buffer and may transfer the detected biosignal to a signal processing unit (not shown).

The shield 230 may surround the electrode face 210 and the pre-amplifier 220 in order to prevent external noise from being picked up by the electrode face 210 and be amplified with the biosignal. For example, the shield 230 may be configured using a conductive material and may block the external noise from entering the FCCE.

The shield 230 may include a flexible material that is sufficiently flexible to conform to an outer shape of the insulator 240. For example, the shield 230 may include a conductive sheet. In the event that the insulator 240 is deformed due to external stress, the shield 230 may be flexible enough to conform to the deformed shape of the insulator 240.

The insulator 240 may support the shield 230 on the electrode face 210. The insulator 240 may be made of a flexible material. To support the shield 230, the insulator 240 may have stiffness and mechanical strength sufficient to maintain a space predefined between the electrode face 210 and the shield 230. The insulator 240 may include air layers, air bubbles or air gaps. The insulator 240 may be made of a material having a micro structure in which an air layer is included. For example, the insulator 240 may be formed of a porous material in which air bubbles are dispersed, such as in a synthetic foam. For example, the insulator 240 may include a silicon foam, an urethane foam, or the like. A material that may form the insulator 240 is further described with reference to FIG. 5.

The conductive foam 250 may enable a contact surface to closely contact an irregular surface. In the event that the metal flat electrode face 210 is attached to an irregular surface such as, for example, a human body, a partial gap may occur between the electrode face 210 and a portion of the body to be measured due to the natural curve of the body unless the conductive foam 250 is used. Such a gap may reduce a capacitance of the capacitive coupling generated between the human body and the electrode face 210. In the event that a biosignal is measured under such a condition, a gain with respect to a frequency response may be decreased.

Thus, according to various examples, the electrode face 210 of the FCCE may include a conductive foam 250, and the conductive foam 250 may reduce the effects of having an irregular or uneven measurement surface. For example, the conductive foam 250 enables the electrode face 210 to closely contact the portion of the body to be measured. Thus, a capacitance component between the human body and the electrode face 210 may be maximized Due to the maximization of the capacitance component, the gain with respect to the frequency response may be increased during the biosignal measurement. Further, even when the human body is in an unstable state such as when the patient is exercising or moving the body, due to a close contact with the portion to be measured, the biosignal may be measured with relative stability.

Figure 3:
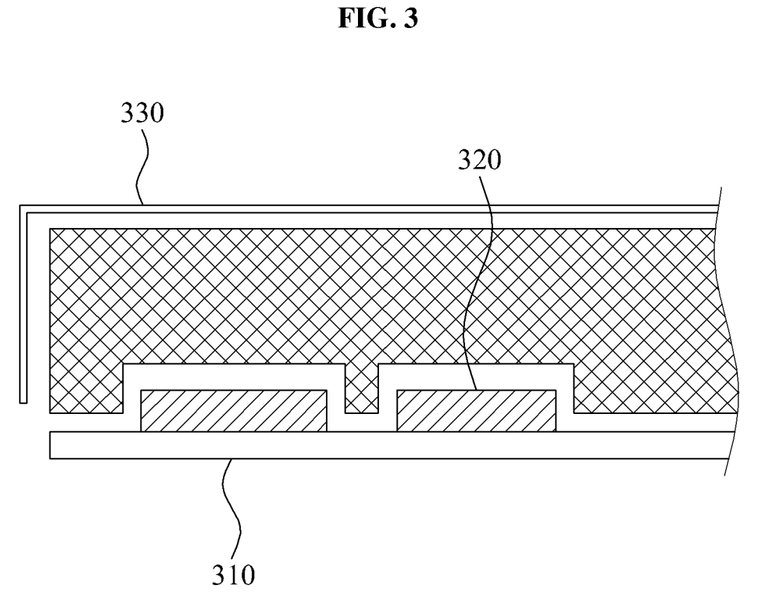
FIG. 3 is a cross-sectional view illustrating another example of an FCCE.

FIG. 3 illustrates another example of an FCCE. Referring to FIG. 3, the FCCE includes an electrode face 310, a pre-amplifier 320, and a shield 330. The configuration of the FCCE may be similar to the aforementioned configuration of the CCE of FIG. 2. Thus, descriptions that are repetitive were omitted for conciseness.

The FCCE may include at least one pre-amplifier 320 on the electrode face 310. In the example illustrated in FIG. 3, two pre-amplifiers 320 are disposed on the electrode face 310.

Figure 4A:
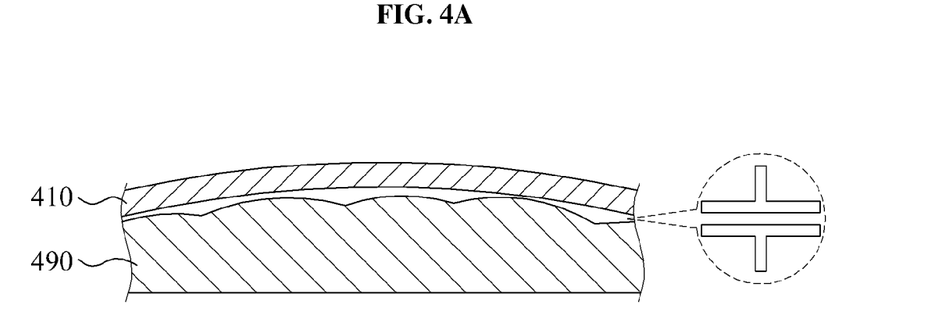
FIG. 4A is a cross-sectional view illustrating an example of an FCCE without a conductive foam.
Figure 4B:
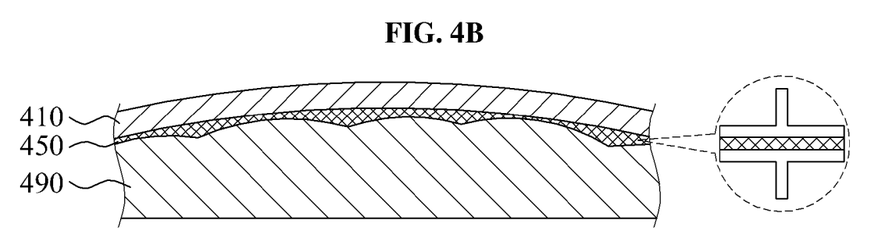
FIG. 4B is a cross-sectional view illustrating an example of an FCCE with a conductive foam.

FIG. 4A illustrates an example of an FCCE without a conductive foam, and FIG. 4B illustrates an example of an FCCE that includes a conductive foam 450. Based on one design, the FCCE may be configured to allow the use of a conductive foam 450 in the FCCE. In the event that a conductive foam 450 is included in the FCCE, a relatively high gain may be achieved in a frequency response curve of a biosignal measurement compared to an FCCE without the conductive foam 450. The high gain may be useful in measuring a change in capacitance between a human body 490 and an electrode face 410; thus, the use of the conductive foam 450 may facilitate the measurement of a biosignal.

As illustrated in FIG. 4B, the conductive foam 450 enables a surface of the electrode face 410 to closely contact an irregular contact surface of the human body 490. Since the surface of the electrode face 410 closely contacts the contact surface of the human body 490 through the conductive foam 450, a dielectric constant between the electrode face 410 and the human body 490 may increase and an interval therebetween may decrease. Accordingly, the capacitance of capacitive coupling between the electrode face 410 and the human body 490 may increase. A frequency response gain may increase in response to the maximization of a capacitance component between the electrode face 410 and the human body 490. Thus, it is possible to measure the biosignal with improved accuracy.

Figure 5:
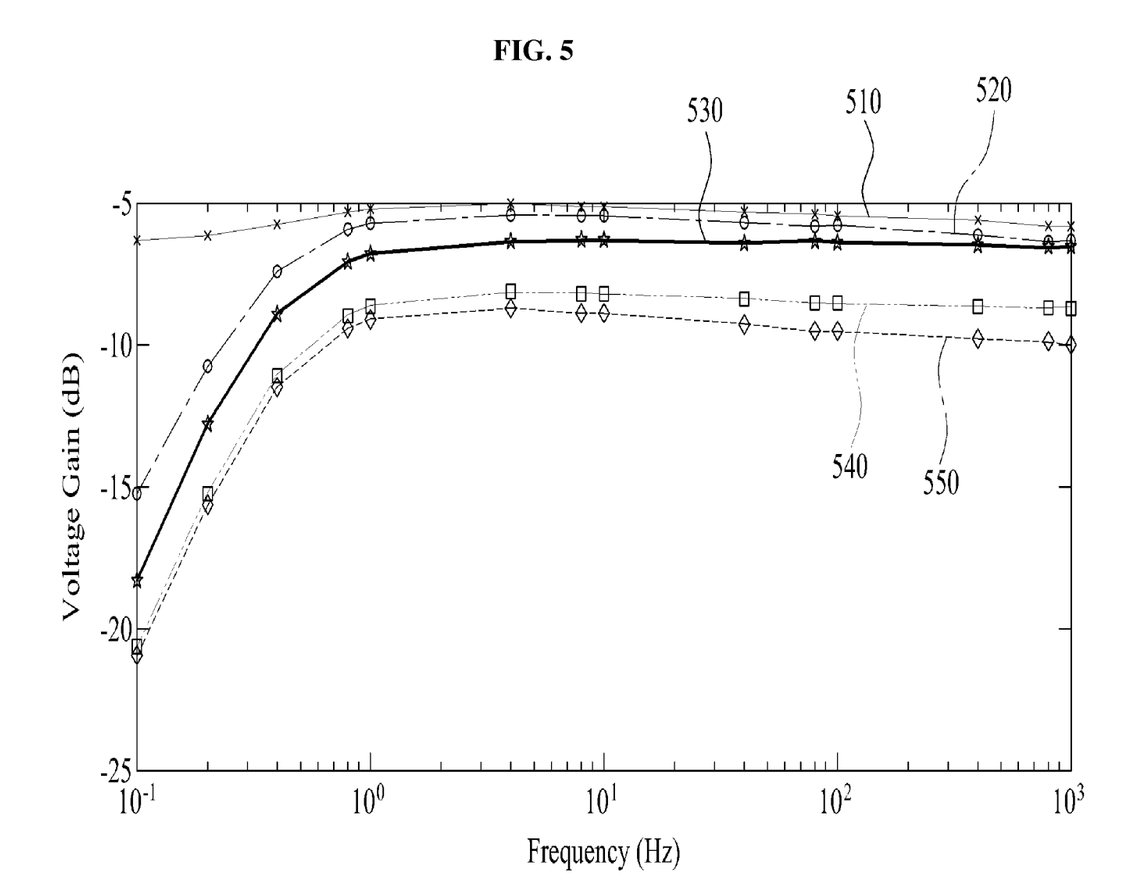
FIG. 5 is a graph illustrating an example of a frequency response curve with respect to a material of an insulator.

FIG. 5 illustrates an example of a frequency response curve with respect to a material of an insulator. External noise may be more effectively eliminated by a shield according to a decrease in a dielectric constant of the insulator. For example, a material having a small dielectric constant that may be used as an insulator of the FCCE include a silicon foam 550, a urethane foam, silicon 540, urethane 520, rubber 530, and polyvinyl chloride (PVC) 510.

The graph of FIG. 5 illustrates the voltage gain obtained with an FCCE that includes an insulator using the aforementioned material during a frequency response evaluation. A relatively small voltage gain was achieved in an order of the PVC 510, the urethane 520, the rubber 530, the silicon 540, and the silicon foam 550. Even though the same material is used, the porous silicon foam 550 including a plurality of air layers may have a relatively small voltage gain compared to the silicone 540. Referring to the graph of FIG. 5, the silicon foam 550 has the smallest voltage gain and has the smallest dielectric constant. Accordingly, among the tested materials, the silicon foam 550 may be the most suitable material for use as the insulator in the FCCE.

In one example, the dielectric constant of the insulator may be less than a predetermined value. For example, the electric constant of the insulator may be less than 12 (silicon), 7 (rubber), 4 or 2 under standard temperature and pressure.

A porous insulator may be used in order to maintain a small dielectric constant and to maintain a shape of an FCCE. A shield of the FCCE may include a conductive sheet for the flexibility. A conductive sheet may not have sufficient strength to maintain the shape of the shield. Accordingly, without using a separate supporting member, parasitic capacitance $C_B$ between an electrode face and the shield may easily vary, and it may be difficult to stably measure the biosignal. A porous material including an air layer that has sufficient stiffness and strength capable of maintaining a predetermined shape and space while having a small dielectric constant, may be used as the insulator.

For example, the silicon foam 550 may have strength capable of maintaining a predetermined space between the electrode face and the conductive sheet provided in a fabric shape, may have a small dielectric constant, and may be flexible. Also, as illustrated in FIG. 5, the silicon foam 550 has the smallest dielectric constant, and may be thus most suitable as a material for the insulator of the FCCE.

According to another example, the insulator may include a material having a dielectric constant less than a predetermined value. The predetermined value may include a dielectric constant of a level at which external noise coming from the shield is sufficiently attenuated while passing through the insulator, and thus allowing a biosignal to be detected. For example, a small dielectric constant may be advantageous in shielding the external noise. Thus, the predetermined value may be a value less than or equal to at least one dielectric constant of the silicon foam 550, the urethane foam, the silicon 540, the urethane 520, the rubber 530, and the PVC 510.

Figure 6A:
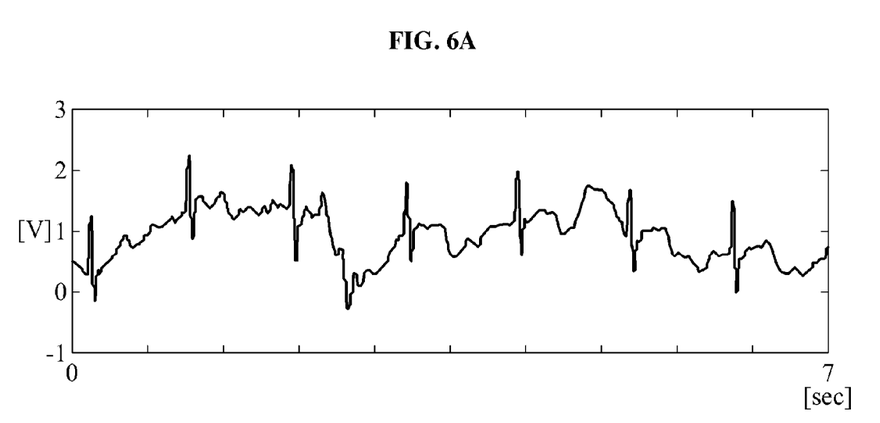
FIG. 6A is a graph illustrating an example of a biosignal measured with an FCCE.
Figure 6B:
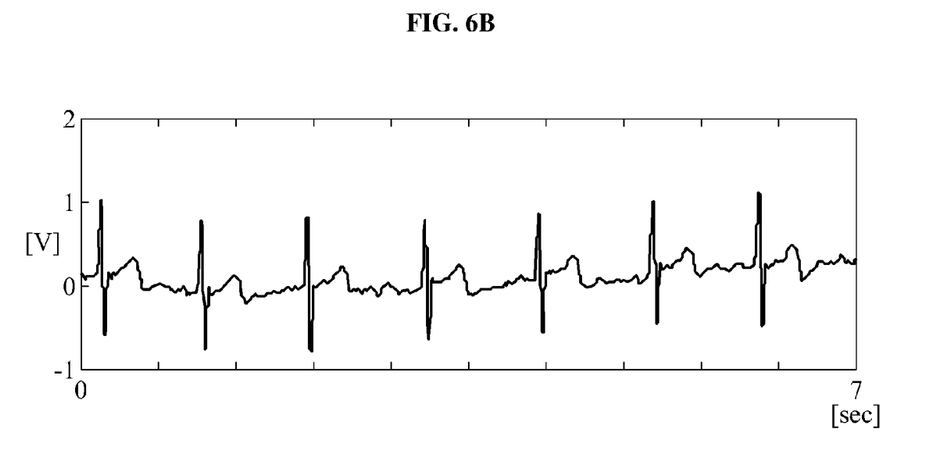
FIG. 6B is a graph illustrating an example of a biosignal measured with an inflexible electrode using a direct contact method.

FIGS. 6A and 6B illustrate an example of a biosignal measured at an FCCE. FIG. 6A illustrates a graph showing an ECG wavelength measured at the FCCE for seven seconds. FIG. 6B illustrates a graph showing an ECG wavelength measured at an inflexible metal electrode for seven seconds using a direct skin contact method.

The FCCE according to examples described above may result in an ECG in which a baseline drift of the ECG wavelength has occurred, as illustrated in the graph of FIG. 6A. The baseline drift can be determined by comparison the graph of FIG. 6A with the graph in FIG. 6B that obtained using direct skin contact. Such baseline drift may be corrected. For example, in an R-peak based application field, an R peak may be sufficiently detected from the waveform obtained with an FCCE, and a baseline drift may be removed by employing an HBP filter at a signal processing unit of a biosignal measurement device.

Figure 7:
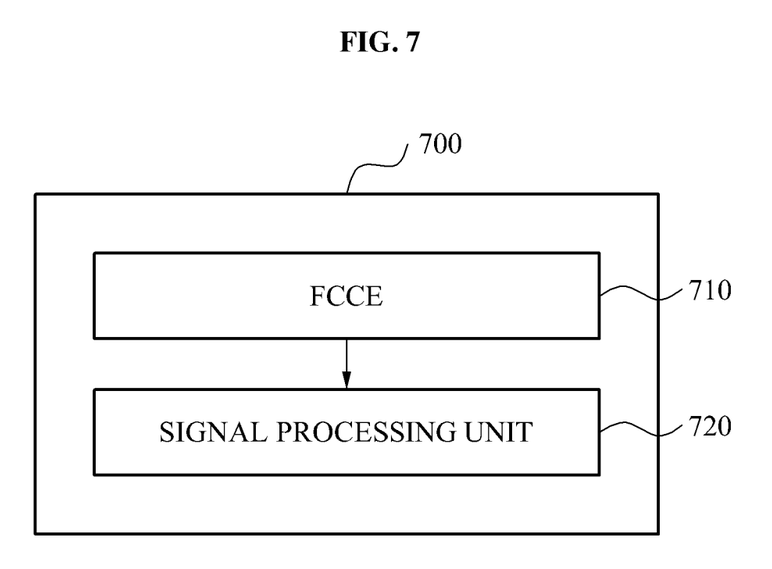
FIG. 7 is a block diagram illustrating an example of a biosignal measurement device.

FIG. 7 illustrates an example of a biosignal measurement device 700. Referring to FIG. 7, the biosignal measurement device 700 includes an FCCE 710 and a signal processing unit 720.

The FCCE 710 may include an insulator configured to support a shield that surrounds a pre-amplifier on an electrode face configured to detect a biosignal. The FCCE 710 may be flexible. The configuration of the FCCE 710 may be similar to the aforementioned configuration of the FCCE in FIG. 2.

The signal processing unit 720 may extract a measurement result by processing the biosignal detected by the FCCE 710. The measurement result may refer to a result of processing the biosignal and may include an ECG wavelength, an EOG wavelength, an EMG wavelength, and an EEG wavelength. For example, the signal processing unit 720 may include an amplifier and a filter configured to process the biosignal. The filter may include an HBP filter and an LBP filter.

The signal processing unit 720 may include a processing device. Further, the biosignal processed by the signal processing unit 720 may be displayed on a display screen, further processed or transmitted to other devices, or transmitted over an IT-network to allow healthcare providers to monitor a patient condition.

A general rigid electrode may not be directly applied to the skin or may not be readily applied to a fabric. However, the biosignal measurement device 700 includes an FCCE 710. Thus, the biosignal may be measured readily by applying the FCCE 710 directly to the skin or indirectly to the skin, through a fabric, a clothing or the like.

Also, with the use of the FCCE 710, the biosignal measurement device 700 may prevent skin irritations or discomfort that may occur while placing a rigid metal material directly on the skin during the measurement of a biosignal.

The FCCE 710 may maintain a predetermined space between an electrode face and a shield including a conductive sheet. By preventing a change in an interval, an effect of parasitic capacitance may be decreased. For example, an insulator having an insulating performance within the FCCE 710 may support the space between the electrode face and the shield.

The FCCE 710 may not use a rigid metal electrode. Thus, the irritation and discomfort of having a direct contact with a rigid metal electrode may be avoided. Further, the FCCE 710 may also be robust against dynamic noise of a biosignal caused by a motion of a human body. Accordingly, the FCCE 710 may be used in a variety of application fields that uses a biosignal. For example, due to enhanced convenience in measurement, a biosignal may be measured without self-awareness of a measurement target. Thus, the measurement of the biosignal can be taken constantly while the patient engages in daily activities. Further, as the design of the device is robust against human motion, the FCCE 710 may be applied to various applications, such as an R-peak based heartbeat monitoring device, a sleepiness prevention device, a daily sleep and stress monitoring device, and a companion animal monitoring device.

The units as described herein may be implemented using hardware components and software components. For example, microphones, amplifiers, band-pass filters, audio to digital convertors, and processing devices may be included in such units. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. In particular, the software and data may be stored by one or more computer readable recording mediums.

Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of non-transitory computer-readable storage media include magnetic media, such as hard disks, floppy disks, and magnetic tape;

optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files including higher level code that may be executed by the computer using an interpreter. The program instructions, that is, software, may be distributed over network coupled computer systems so that the software is stored and executed in a distributed fashion. For example, the software and data may be stored by one or more computer readable storage mediums. Also, functional programs, codes, and code segments that accomplish the examples disclosed herein can be easily construed by programmers skilled in the art to which the examples pertain based on and using the flow diagrams and block diagrams of the figures and their corresponding descriptions as provided herein. Also, the described unit to perform an operation or a method may be hardware, software, or some combination of hardware and software. For example, the unit may be a software package running on a computer or the computer on which that software is running.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A capacitively-coupled active electrode, comprising:
an electrode face configured to detect a biosignal;
a pre-amplifier configured to amplify the biosignal;
a shield configured to surround the electrode face and the pre-amplifier; and
an insulator that is flexible and configured to support the shield on the electrode face,
wherein the insulator comprises a porous material in which air bubbles are dispersed, and
wherein the electrode face comprises a conductive foam configured to conform to an irregular contact surface of a target.

2. The electrode of claim 1, wherein the insulator comprises a material having mechanical strength to maintain a space predefined between the electrode face and the shield.

3. The electrode of claim 1, wherein the insulator comprises at least one of silicon foam, urethane foam, silicone, urethane, rubber, and polyvinyl chloride (PVC).

4. The electrode of claim 1, wherein the insulator comprises a material having a dielectric constant less than 4 under standard temperature and pressure.

5. The electrode of claim 1, wherein the shield comprises a flexible material that conforms to a shape of the insulator.

6. The electrode of claim 1, wherein the shield comprises a conductive sheet that surrounds the insulator.

7. The electrode of claim 1, wherein the electrode face comprises a flexible printed circuit board (FPCB) that conforms to a shape of the insulator.

8. The electrode of claim 1, wherein the electrode face is further configured to detect the biosignal without a conductive gel disposed on the electrode face.

9. A biosignal measurement device, comprising:
a capacitively-coupled active electrode comprising an insulator that is flexible and configured to support a shield that surrounds a pre-amplifier on an electrode face configured to detect a biosignal; and
a signal processing unit configured to extract a measurement result by processing the biosignal,
wherein the insulator comprises a porous material in which air bubbles are dispersed, and
wherein the electrode face comprises a conductive foam configured to conform to an irregular contact surface of a target to establish a non-contact capacitive coupling.

10. The device of claim 9, wherein the insulator comprises a material having mechanical strength to maintain a space predefined between the electrode face and the shield.

11. The device of claim 9, wherein the insulator comprises at least one of silicon foam, urethane foam, silicone, urethane, rubber, and polyvinyl chloride (PVC).

12. The device of claim 9, wherein the insulator comprises a material having a dielectric constant less than 4 under standard temperature and pressure.

13. The device of claim 9, wherein the shield comprises a flexible material that conforms to a shape of the insulator.

14. The device of claim 9, wherein the shield comprises a conductive sheet that surrounds the insulator.

15. The device of claim 9, wherein the electrode face comprises a flexible printed circuit board (FPCB) that conforms to a shape of the insulator.

16. The device of claim 9, wherein the electrode face is further configured to detect the biosignal without a conductive gel disposed on the electrode face.

17. A capacitively-coupled electrode, comprising:
an electrode face configured to form a capacitive coupling with a subject in a non-contact manner to detect a biosignal; and
a pre-amplifier disposed on a rear side of the electrode face and embedded in a porous insulator,
wherein the electrode face comprises a conductive foam configured to conform to an irregular contact surface of a target to establish a non-contact capacitive coupling.

18. The capacitively-coupled electrode of claim 17, further comprising a shield covering the porous insulator such that the pre-amplifier is encapsulated between the rear side of the electrode face and the shield.

19. The capacitively-coupled electrode of claim 18, wherein the shield comprises a flexible material that conforms to a shape of the porous insulator.

* * * * *